United States Patent [19]

Almgren et al.

[11] Patent Number: 5,055,490

[45] Date of Patent: Oct. 8, 1991

[54] STEREOISOMERS OF BENZONITRILE DERIVATIVES, USEFUL AS CARDIAC ARRHYTHMIAC AGENTS

[75] Inventors: Olle K. S. Almgren, Göteborg; Kjell H. Andersson, Fjärås; Göran B. D. Duker, Frölunda; Bo R. Lamm, Göteborg; Gert C. Strandlund, Mölndal, all of Sweden

[73] Assignee: Aktiebolaget Hassle, Mölndal, Sweden

[21] Appl. No.: 539,852

[22] Filed: Jun. 18, 1990

[30] Foreign Application Priority Data

Jun. 20, 1989 [SE]  Sweden ............................... 8902237

[51] Int. Cl.$^5$ .................. A61K 31/10; A61K 31/045; C07C 255/50
[52] U.S. Cl. ..................................... 514/524; 558/413
[58] Field of Search ......................... 558/413; 514/524

[56] References Cited

PUBLICATIONS

Almgren et al., Chem. Abstracts, vol. 112, No. 1; 7180y (1990).

*Primary Examiner*—Johann Richter
*Attorney, Agent, or Firm*—White & Case

[57] ABSTRACT

4-[3-[ethyl[3-((R*)-propylsulfinyl)propyl]amino]-2(R)-hydroxypropoxy]-benzonitrile,
4-[3-[ethyl[3-((S*)-propylsulfinyl)propyl]amino]-2(R)-hydroxypropoxy]-benzonitrile,
4-[3-[ethyl[3-((R*)-propylsulfinyl)propyl]amino]-2(S)-hydroxypropoxy]-benzonitrile,
4-[3-[ethyl[3-[((S*)-propylsulfinyl)propyl]amino]-2(S)-hydroxypropoxy]-benzonitrile and pharmaceutically acceptable salt thereof, processes for their preparation, as well as the use of said compounds for the preparation of medicaments with action against cardiac arrhythmias.

10 Claims, No Drawings

5,055,490

STEREOISOMERS OF BENZONITRILE DERIVATIVES, USEFUL AS CARDIAC ARRHYTHMIAC AGENTS

FIELD OF THE INVENTION

The present invention relates to stereoisomers of the compound 4-[3-[ethyl[3-(propylsulfinyl)propyl]amino]-2-hydroxypropoxy]-benzonitrile, its preparation and use.

BACKGROUND OF THE INVENTION

Our prior patent application PCT/SE88/00691, filed on Dec. 20, 1988 and published after the filing date of this application, relates to a group of novel compounds which are useful in the treatment, acute as well as long term, of cardiac arrhythmias of diverse etiology. Among the compounds included in the group of compounds disclosed in said application is the compound 4-[3-[ethyl[3-(propylsulfinyl)propyl]amino]-2-hydroxypropoxy]-benzonitrile having the formula I

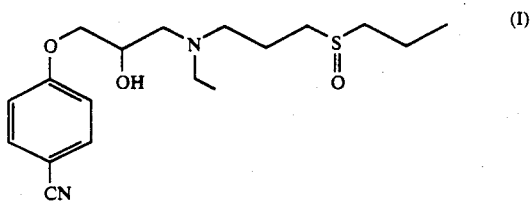
(I)

which can be obtained as a stereoisomeric mixture as well as in the form of the different isomers; the following two stereoisomers are mentioned in the said application:

4-[3-[ethyl[3-(propylsulfinyl)propyl]amino]-2(R)-hydroxypropoxy]-benzonitrile,

4-[3-[ethyl[3-(propylsulfinyl)propyl]amino]-2(S)-hydroxypropoxy]-benzonitrile.

THE INVENTION

The compound of the formula I having two chiral centra (*)

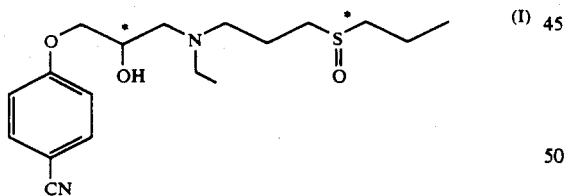
(I)

It has now been found that the stereoisomers of the compound of formula I above i.e.

4-[3-[ethyl[3-((R*)-propylsulfinyl)propyl]amino]-2(R)-hydroxypropoxy]-benzonitrile, 4-[3-[ethyl[3-((S*)-propylsulfinyl)propyl]amino]-2(R)-hydroxypropoxy]-benzonitrile, 4-[3-[ethyl[3-((R*)-propylsulfinyl)propyl]amino]-2(S)-hydroxypropoxy]-benzonitrile 4-[3-[ethyl[3-((S*)-propylsulfinyl)propyl]amino]-2(S)-hydroxypropoxy]-benzonitrile, and pharmaceutically acceptable salts thereof, are valuable new products useful for treatment, acute as well as long term, of cardiac arrhythmias of diverse etiology.

An object is to provide antiarrhythmics which have less prominent side effects than existing antiarrhythmic drugs. The compounds should for instance be free of negative inotropic effect and the compounds may even be positively inotropic. The compounds should further separate the anti-arrhythmic effect from central nervous and gastrointestinal effects.

The stereoisomers of this invention may be used therapeutically in the stereochemical pure forms.

The present invention also relates to processes for the preparation of said isomers according to the present invention.

A. The compounds of the formula

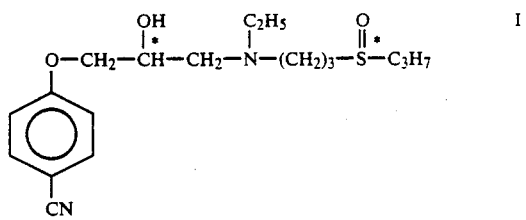
I can be prepared by reaction of a compound of the formula

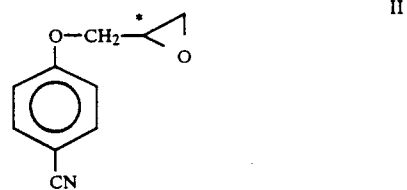
II with a compound of the formula

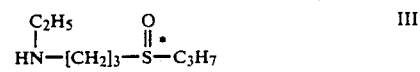
III

The reaction is typically carried out in a suitable solvent such as isopropanol or N,N-dimethylformamide. The mixture should be heated to a temperature in the range 40°–100° C. until the reaction is completed. Thereafter the product can be isolated by conventional methods; or B. A compound of the formula

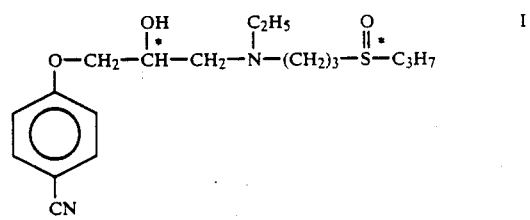
I can be prepared by reacting a compound of the formula

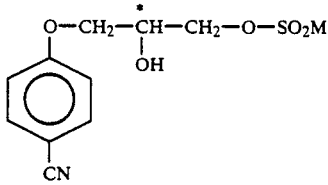

where M is methyl or a 4-methyl-phenyl residue, with a compound of the formula

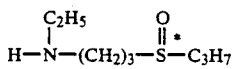

The reaction is typically carried out in a suitable organic solvent such as acetonitrile or N,N-dimethylformamide. A suitable organic or inorganic base such as triethylamine or potassium carbonate is added to the mixture. The mixture is then heated to a temperature in the range of 90°–100° C. until the reaction is completed after which the products can be isolated and purified by conventional methods.

The invention further relates to a method of preventing or reducing cardiac arrhythmias in mammals, including man, which comprises administering to a host in need of such treatment an effective amount of said stereoisomer of the compound of the formula I or pharmaceutically acceptable salts thereof.

The invention yet further relates to said stereoisomers of the compound of the formula I or pharmaceutically acceptable salts thereof for use as a medicament, particularly as an antiarrhythmic agent.

The invention also relates to the use of the stereoisomers of the compound of the formula I for the manufacture of medicaments with action against cardiac arrhythmias.

The following non-limiting examples further illustrate the invention.

EXAMPLE 1

4-[3-[ethyl[3-((S*)-propylsulfinyl)propyl]amino]-2(R)-hydroxypropoxy]-benzonitrile a) Ethyl(3-(S*)-propylsulfinyl)propylamine A hot solution of 27.2 g (0.1 mol) of (−)-1,3,2-dioxaphosphorinane-5,5-dimethyl-2-hydroxy-4-(2-methoxyphenyl)-2-oxide and 17.73 g (0.1 mol) of racemic ethyl (3-propylsulfinyl)-propylamine in 750 ml of acetone and 32.5 ml of methanol was allowed to cool to room temperature, yielding 23.9 g of crystalline material. The experiment was repeated on a 0.25 mol scale, this time yielding 53.0 g of crystals. The combined crops were recrystallized five times from acetone-methanol, finally yielding 8.95 g of salt.

A solution of 15.06 g (0.0392 mol) of trioctylamine in dichloromethane was shaken with 19.6 ml of 2M hydrochloric acid. The phases were separated and the organic layer was washed with water. The organic phase, now containing trioctylammonium chloride, was stirred for 90 min. with a solution of 8.8 g (0.0196 mol) of the above mentioned resolved salt in water. The phases were separated, and the organic layer was washed with water. The combined aqueous phases were washed with dichloromethane, and then brought to pH 11.5 with 10M sodium hydroxide. Extraction four times with dichloromethane yielded 2.3 g of laevorotatory amine base, arbitrarily denoted S* $[\alpha]_D^{20} -8.0°$ (c=1, CH$_3$OH).

$^{13}$C NMR (as salt with (−)-1.3.2-dioxaphosphorinane-5,5-dimethyl-2-hydroxy-4-(2-methoxyphenyl)-2-oxide); in CDCl$_3$: 10.80, 12.95, 15.81, 17.55, 19.49, 19.58, 20.41, 36.59, 36.61, 42.37, 45.50, 48.73, 53.67, 54.71, 76.79, 76.83, 77.34, 109.63, 119.69, 126.42, 126.50, 128.33, 128.93, 155.83.

b) (R)-4-(oxiranylmethoxy)-benzonitrile

A solution of 2.71 g of (2S)-1-(4-cyanophenoxy)-3-methanesulfonyloxypropan-2-ol in 40 ml of 1,2-dimethoxyethane was stirred with 1.0 g of powdered sodium hydroxide at room temperature for 22 h. 10 ml of saturated sodium chloride solution was added, and the mixture was extracted twice with ether. Washing with 5% sodium hydrogen carbonate, drying over magnesium sulfate, filtration and evaporation gave 1.76 g of crystalline material, m.p. 67.5° C., $[\alpha]_D^{20} -14.7°$ (c=1, acetone)

NMR: $^{13}$C in CDCl$_3$; 44.40, 49.71, 69.02, 104.59, 115.34, 118.95, 133.98, 161.66 ppm.

c)
4-[3-[ethyl[3-((S*)-propylsulfinyl)propyl]amino]-2(R)-hydroxypropoxy]-benzonitrile A mixture of 3 g of ethyl(3-(S*)-propylsulfinyl)-propylamine and 3.18 g of (R)-4-(oxiranylmethoxy)-benzonitrile was refluxed for 16 h in 25 ml of isopropyl alcohol. After evaporation of the solvent, the crude product was dissolved in 2M hydrochloric acid, washed with ether, the solution brought to pH 11.5 with 2M sodium hydroxide and extracted with dichloromethane. Evaporation of the organic phase gave 6.11 g of an oil.

$^{13}$C NMR in CDCl$_3$: 11.23, 13.17, 16.08, 20.46, 47.41, 49.98, 52.41, 54.46, 56.11, 66.05, 70.50, 103.80, 115.13, 118.92, 133.69, 161.92 ppm.

EXAMPLE 2

4-[3-[ethyl[3-((R*)-propylsulfinyl)propyl]amino]-2-(S)-hydroxypropoxy]-benzonitrile a) Ethyl(3-(R*)-propylsulfinyl)propylamine Resolution of racemic ethyl (3-propylsulfinyl)-propylamine with (+)-1,3,2-dioxaphosphorinane-5,5-dimethyl-2-hydroxy-4-(2-methoxyphenyl)-2-oxide in analogy with example 1a gave dextrorotatory amine base. This compound, arbitrarily denoted R*, has the following data: $[\alpha]_D^{20} +7.6°$ (c=1, CH$_3$OH)

$^{13}$C NMR (as salt with (+)-1,3,2-dioxaphosphorinane-5,5-dimethyl-2-hydroxy-4-(2-methoxyphenyl)-2-oxide); in CDCl$_3$: 10.92, 13.07, 15.93, 17.66, 19.56, 19.70, 20.52, 36.72, 36.73, 42.48, 45.61, 48.85, 53.79, 54.82, 76.92, 76.96, 77.45, 77.49, 109.73, 119.81, 126.54, 126.62, 128.44, 129.06, 155.95.

b) (S)-4-(oxiranylmethoxy)-benzonitrile

From 2.7 g (2R)-1-(4-cyanophenoxy)-3-methanesulfonyloxypropan-2-ol in analogy with example 1b was obtained 1.75 g crystalline material; m.p. 68.0° C. $[\alpha]_D^{20} +14.5°$ (c=1, acetone)

$^{13}$C NMR in CDCl$_3$: 44.21, 49.58, 68.90, 104.25, 115.20, 118.86, 133.80, 161.53.

c)
4-[3-[ethyl[3-((R*)-propylsulfinyl)propyl]amino]-2(S)-hydroxypropoxy]-benzonitrile A mixture of 2.3 g of ethyl(3-(R*)-propylsulfinyl)-propylamine and 3.18 g of (S)-4-(oxiranylmethoxy)-benzonitrile in 19 ml of isopropyl alcohol was refluxed 16 h and thereafter worked up in analogy with 1c yielding 4.1 g of an oil; $[\alpha]_D^{20} + 26.5°$ (c=1, CH$_3$OH)

$^{13}$C NMR in CDCl$_3$: 11.16, 13.05, 15.96, 20.37, 47.38, 49.87, 52.37, 54.31, 56.05, 66.10, 70.47, 103.65, 115.06, 118.78, 133.55, 161.86.

EXAMPLE 3

4-[3-[ethyl[3-((R*)-propylsulfinyl)propyl]amino]-2(R)-hydroxypropoxy]-benzonitrile A mixture of 2.3 g of ethyl/(R*)-3-propylsulfinyl/-propylamine and 2.5 g of (R)-4-(oxiranylmethoxy)-benzonitrile was refluxed for 16 h in 19 ml of isopropyl alcohol in analogy with example 1c. Traditional work up procedures gave 4.27 g of an oil; $[\alpha]_D^{20} - 13.4°$ (c=1, CH$_3$OH)

$^{13}$C NMR in CDCl$_3$: 11.58, 13.36, 16.29, 20.57, 47.70, 49.96, 52.41, 54.64, 56.36, 66.24, 70.63, 104.18, 115.33, 119.07, 133.91, 162.09.

EXAMPLE 4

4-[3-[ethyl[3-((S*)-propylsulfinyl)propyl]amino]-2(S)-hydroxypropoxy]-benzonitrile A mixture of 2.3 g of ethyl[3-(S*)-propylsulfinyl]-propylamine and 2.5 g of (S)-4-(oxiranylmethoxy)-benzonitrile in 19 ml of isopropyl alcohol was refluxed for 24 h in analogy with example 1c. Traditional work up procedures gave 3.65 g of an oil; $[\alpha]_D^{20} + 11.1°$ (c=1, CH$_3$OH)

$^{13}$C NMR in CDCl$_3$: 11.56, 13.33, 16.25, 20.54, 47.71, 49.92, 52.42, 54.53, 56.31, 66.33, 70.64, 104.03, 115.33, 119.06, 133.86, 162.11.

We claim:
1. A compound having the formula I

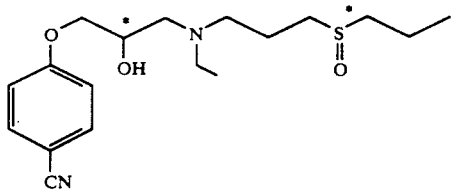
(I)

in the form of one of the stereoisomers:
4-[3-[ethyl[3-((R*)-propylsulfinyl)propyl]amino]-2(R)-hydroxypropoxy]-benzonitrile,
4-[3-[ethyl[3-((S*)-propylsulfinyl)propyl]amino]-2(R)-hydroxypropoxy]-benzonitrile,
4-[3-[ethyl[3-((R*)-propylsulfinyl)propyl]amino]-2(S)-hydroxypropoxy]-benzonitrile, and
4-[3-[ethyl[3-((S*)-propylsulfinyl(propyl]amino]-2(S)-hydroxypropoxy]-benzonitrile, or a pharmaceutically acceptable salt thereof.

2. A compound 4-[3-[ethyl[3-((R*)-propylsulfinyl)propyl]amino]-2(R)-hydroxypropoxy]-benzonitrile, or a pharmaceutically acceptable salt thereof.

3. A compound 4-[3-[ethyl[3-((S*)-propylsulfinyl)propyl]amino]-2(R)-hydroxypropoxy]-benzonitrile, or a pharmaceutically acceptable salt thereof.

4. A compound 4-[3-[ethyl[3-((R*)-propylsulfinyl)propyl]amino]-2(S)-hydroxypropoxy]-benzonitrile, or a pharmaceutically acceptable salt thereof.

5. A compound 4-[3-[ethyl[3-((S*)-propylsulfinyl)propyl]amino]-2(S)-hydroxypropoxy]-benzonitrile, or a pharmaceutically acceptable salt thereof.

6. A method for the treatment of cardiac arrhythmia in mammals comprising the administration to a host in need of such treatment of an effective amount of a compound according to any one of claims 1-5, or a pharmaceutically acceptable salt thereof.

7. A method according to claim 6 wherein the compound is 4-[3-[ethyl[3-((R*)-propylsulfinyl) propyl]amino]-2(R)-hydroxypropoxy]-benzonitrile, or a pharmaceutically acceptable salt thereof.

8. A method according to claim 6 wherein the compond is 4-[3-[ethyl[3-((S*)-propylsulfinyl)propyl] amino]-2(R)-hydroxypropoxy]-benzonitrile, or a pharmaceutically acceptable salt thereof.

9. A method according to claim 6 wherein the compound is 4-[3-[ethyl[3-((R*)-propylsulfinyl) propyl]amino]-2(S)-hydroxypropoxy]-benzonitrile or a pharmaceutically acceptable salt thereof.

10. A method according to claim 6 wherein the compound is 4-[3-[ethyl[3-((S*)-propylsulfinyl) propyl]amino]-2(S)-hydroxypropoxy]-benzonitrile or a pharmaceutically acceptable salt thereof.

* * * * *